(12) United States Patent
Hariharan et al.

(10) Patent No.: US 10,179,157 B2
(45) Date of Patent: Jan. 15, 2019

(54) **SLIM AND AQUA CONCENTRATE HAVING STANDARDIZED AND TRIPLE SALT STABILIZED (−)-HYDROXYCITRIC ACID FROM *GARCINIA CAMBOGIA* EXTRACT FOR MAKING CONCENTRATE AND SLIMMING WATER AND THEIR DERIVED PRODUCT FOR WEIGHT MANAGEMENT**

(71) Applicant: Phytotech Extracts Private Limited, Bangalore (IN)

(72) Inventors: Venkatachalam Hariharan, Bangalore (IN); PradeepKumar Siddavvanahalli Virupakshappa, Bangalore (IN); Kanchana Hariharan, Bangalore (IN); Vinayaka Neechadi Puppadar, Bangalore (IN); Paranjothi Kanni, Bangalore (IN)

( * ) Notice: Subject to any disclaimer, the term of this patent is extended or adjusted under 35 U.S.C. 154(b) by 0 days.

(21) Appl. No.: 15/551,234

(22) PCT Filed: Feb. 15, 2016

(86) PCT No.: PCT/IB2016/050786
§ 371 (c)(1),
(2) Date: Aug. 15, 2017

(87) PCT Pub. No.: WO2016/132268
PCT Pub. Date: Aug. 25, 2016

(65) Prior Publication Data
US 2018/0028585 A1 Feb. 1, 2018

(30) Foreign Application Priority Data

Feb. 16, 2015 (IN) .............................. 749/CHE/2015

(51) Int. Cl.
*A61K 36/00* (2006.01)
*A61K 36/38* (2006.01)
*A61K 31/194* (2006.01)

(52) U.S. Cl.
CPC ............ *A61K 36/38* (2013.01); *A61K 31/194* (2013.01); *A61K 2236/00* (2013.01); *A61K 2236/331* (2013.01); *A61K 2236/51* (2013.01); *A61K 2236/53* (2013.01)

(58) Field of Classification Search
CPC ....................................................... A61K 36/00
See application file for complete search history.

(56) References Cited

U.S. PATENT DOCUMENTS

| 5,656,314 A | 8/1997 | Moffett |
| 7,208,615 B2 | 4/2007 | Gokaraju |
| 2004/0259937 A1* | 12/2004 | Samuel .................. A61K 31/19 514/460 |

OTHER PUBLICATIONS

Pritam G. Bafna, "Optimization of Process Parameters for Extraction of Kokum (*Garcinia indica*) Fruit Pulp using Response Surface Methodology (RSM)," International Journal of Scientific & Engineering Research vol. 3, Issue 8, Aug. 2012, pp. 1-7.

* cited by examiner

*Primary Examiner* — Qiuwen Mi
(74) *Attorney, Agent, or Firm* — J. Peter Paredes; Rosenbaum IP, P.C.

(57) ABSTRACT

The present invention discloses a slim and aqueous extract of *Garcinia cambogia* comprising (−)-hydroxycitric acid as dietary product for weight management. The present invention also discloses a process of preparation of aqueous extract wherein the *Garcinia cambogia* fruit rinds are subjected to cold circulation to retain the phytochemical components and the aqueous extract is adjusted to neutral pH and stabilized with triple mineral salt of calcium, magnesium and potassium and decolorized using activated carbon. The colorless, odorless aqueous extract obtained is subjected to qualitative and quantitative analysis to obtain pure concentrate, which is useful in food, beverage and pharmaceutical industries as dietary supplement. The concentrate equivalent to 1500 mg of (−)-hydroxycitric acid on dried basis is used for the consumption with the distilled water. The slim and aqueous extract concentrate of *Garcinia cambogia* is useful in treatment of overweight, obesity and hypercholesterolemia.

5 Claims, 1 Drawing Sheet

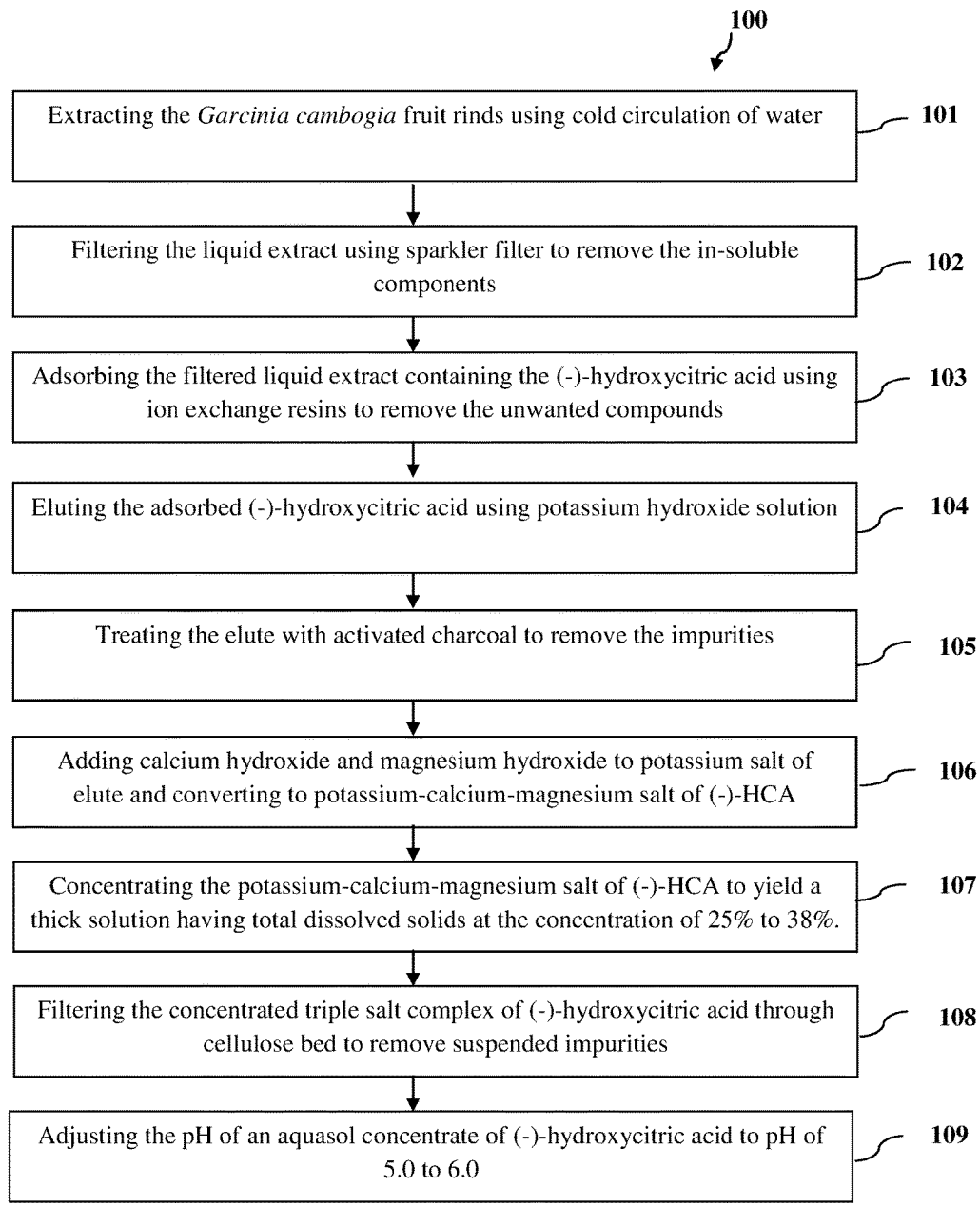

SLIM AND AQUA CONCENTRATE HAVING STANDARDIZED AND TRIPLE SALT STABILIZED (−)-HYDROXYCITRIC ACID FROM *GARCINIA CAMBOGIA* EXTRACT FOR MAKING CONCENTRATE AND SLIMMING WATER AND THEIR DERIVED PRODUCT FOR WEIGHT MANAGEMENT

TECHNICAL FIELD OF THE INVENTION

The present invention relates to a slim and aqueous extract of *Garcinia cambogia* standardized to (−)-Hydroxycitric acid ((−)-HCA) as dietary product for weight management. The aqueous extract is further stabilized with triple salt of calcium, magnesium and potassium, which are essential for various biochemical activities. The invention also relates to a process for preparation of aqueous concentrate extract of *Garcinia cambogia* from the dried fruit rinds, which includes specialized method of extraction, treatment with mineral salts for the stabilization of the (−)-hydroxycitric acid and filtration methods.

BACKGROUND OF THE INVENTION

The prevalence of overweight and obesity has increased over time. One of the major problems in the existing lifestyle is overweight due to lack of energy balance. These conditions may lead to different cardiovascular and other disorders in humans. There are many approaches for weight management to reduce or maintain body weight. However, dietary approaches play a vital role in reducing body weight in human.

The medical and the psychological impact of overweight results in improved dietary and physical activities leading to the use of dietary supplements for weight loss. A wide variety of weight management approaches are presently available. Natural dietary supplements regulate the body metabolism and helps in reducing excess fat without inducing any side effects. Hence, there is a demand for natural and herbal extracts for weight management.

*Garcinia cambogia* is a small, sour fruit of tropical tree native to Southeast Asia and India. It is known in the literature to use the fruit for stomach ulcers and digestive problems. *Garcinia cambogia* is also useful as an ingredient in the Indian food.

(−)-hydroxycitric acid, an active ingredient of the *Garcinia cambogia* is a citric acid derivative, which reduces the fat storage. (−)-hydroxycitric acid blocks fat by inhibiting the activity of citrate lyase and reduce the lipid content in the blood stream. Citrate lyase converts excess sugars and carbohydrates into cholesterol, triglycerides and fatty acids. In addition, (−)-hydroxycitric acid is also effective in reducing the appetite by increasing the serotonin levels. It is known that elevated levels of serotonin promote weight loss by reducing appetite and sugar cravings.

The consumption of *Garcinia cambogia* increases the rate of metabolism. As a result, the energy consumption is more thus using the stored fat as fuel.

The European Patent No. EP0866137A1 titled "Process for producing calcium salt of (−)-Erythrohydroxycitric acid" discloses a process for extraction of calcium salt of hydroxycitric acid from the fruit rind of *Garcinia* species such as *G. cambogia, G. indica* and *G. atrovirdis* using a mixture of pectic enzymes. The calcium salt of hydroxycitric acid is used as an active therapeutic component to alleviate fat formation. The process involves the preparation of aqueous solution of suspension of fruit rinds of *Garcinia* species. The aqueous solution is heated with a pectic enzyme at the temperature of 30° C. to 50° C. Further, the mass is heated to deactivate the enzyme. The pH of the resulting solution is adjusted to 8-11 by adding the aqueous alkaline solution and finally the calcium chloride is added to the alkali solution to form the calcium salt of (−)-erythro-hydroxy acetic acid. However, the invention does not disclose the use of any specific filtration method to obtain a purified product. The active ingredient obtained is in the powdered form, which may be difficult to use as a dietary supplement. Further, the active component is standardized using only a single salt.

The U.S. patent Ser. No. 10/822,867 titled "Hydroxycitric Acid Complex Metal Salts, Composition, and Methods" discloses a tri-, tetra- and penta-metal complex salts of hydroxycitric acid and method of making and using the same. The hydroxycitric acid is isolated from *Garcinia cambogia, G. indica* and *G. atrovirdis*. The product produced is used as a dietary supplement, which is useful in promoting weight loss, preventing weight gain and for other health benefits. The complex metal salt of (−) hydroxycitric acid and its lactone is prepared from aqueous extract of *Garcinia* and a mixture of bases selected from oxides, bicarbonates, carbonates, hydroxides of sodium, potassium, calcium, magnesium and zinc. The aqueous extract of fruit rinds is treated with calcium hydroxycitrate and the pH is adjusted to alkali. The calcium is removed as insoluble calcium sulphite to obtain clear brown liquid of hydroxycitric acid. However, the process does not include any specific method of filtration to obtain a purified product. The invention also does not disclose the stability of the final product.

The U.S. patent Ser. No. 10/425,428 titled "From aqueous extract of *Garcinia cambogia*/indica fruits; tasteless; for use in foods" discloses a pure, stabilized calcium and potassium salts of hydroxycitric acid prepared from *Garcinia cambogia* or *G. indica* fruit extract. The process involves preparation of aqueous extract of *Garcinia* fruit rinds and mixing with trialkylamine. The mixture is treated with potassium or sodium salts to obtain respective hydroxycitric acid salts. The solution is treated with activated charcoal to decolorize the solution. The decolorized solution is treated with calcium chloride to obtain calcium salt of hydroxycitric acid. Finally, the calcium salt of hydroxycitric acid is washed and dried to yield a powder of calcium salt of hydroxycitric acid. The invention does not disclose the use of any specific filtration methods. Moreover, the final product obtained is a single salt of hydroxycitric acid.

There are different formulations of *Garcinia cambogia* available for weight management in the form of tablets, capsules, powder etc., which are single or double salts stabilized and are less effective for weight management. There are different processes available for extraction of active ingredients. However, the existing processes fail to disclose the extraction of active ingredient with cold circulation.

Hence, there is need of formulation of *Garcinia cambogia* for weight management with increased bioavailability.

SUMMARY OF THE INVENTION

The present invention relates to a slim and aqueous extract of *Garcinia cambogia* comprising (−)-hydroxycitric acid as dietary product for weight management. The aquasol concentrate of *Garcinia cambogia* comprises *Garcinia cambogia* fruit rind at the concentration of 725-760 mgml$^{-1}$ of aquasol concentrate.

The lactone form of (−)-hydroxycitric acid is less effective. The aqueous extract comprising (−)-hydroxycitric acid is further stabilized with triple salt of calcium, magnesium and potassium, which are essential for various biochemical activities. The stabilization with triple salts results in more efficacy of the composition.

The invention also relates to a process for preparation of aqueous concentrate extract of *Garcinia cambogia* from the dried fruit rinds, which includes cold circulation method of extraction using cone shaped stainless steel extractor. After extraction, the liquid extract is filtered to remove in-soluble components and the filtrate is adsorbed on ion exchange resins and eluted. The elute is further treated with potassium to form a potassium salt of the filtrate. Potassium salt of the filtrate is further stabilized by addition of calcium hydroxide and magnesium hydroxide to form potassium-calcium-magnesium salt of (−)-hydroxycitric acid. Triple salt of (−)-hydroxycitric acid is concentrated to yield a thick solution with total dissolved solids at the concentration of 25% to 38%. Finally, the concentrated triple salt is filtered and pH of the filtrate is adjusted to 5.0 to 6.0 to form aquasol concentrate.

The aquasol concentrate is filled in bottles and sterilized. 1500 mg of *Garcinia cambogia* extract in two to three divided pre-prandial doses per day is recommended for weight management. The aquasol concentrate of *Garcinia cambogia* showed a shelf-life of minimum 18 months.

The slim and aqueous concentrate of *Garcinia cambogia* extract is natural, herbal product and consumer friendly dietary supplement for weight management. *Garcinia cambogia* extract is easily miscible with water or any solution. It is useful in beverage industry, pharmaceutical and is enriched with the optimum range of mineral salts for weight management, hypercholesterolemia etc.

BRIEF DESCRIPTION OF THE DRAWINGS

The foregoing and other features of various embodiments will become more apparent from the following detailed description of embodiments when read in conjunction with the accompanying drawing.

FIG. 1 illustrates a flow chart for a process of preparation of aquasol concentrate of *Garcinia cambogia*.

DETAILED DESCRIPTION OF THE INVENTION

In order to more clearly and concisely describe and point out the subject matter of the claimed invention, the following definitions are provided for specific terms, which are used in the following written description.

The term "Diet" means a special course of food to which a person restricts himself, either to lose weight or for medical reasons.

The term "Filtration" means mechanical or physical operation, which is used for the separation of solids from fluids (liquids or gases) by interposing a medium through which only the fluids can pass.

The term "Aqueous extract" means a water-based preparation of a plant substance containing the biologically active portion of the plant or substance without its cellular residue.

The present invention relates to a slim and aqueous extract of *Garcinia cambogia* called as aquasol concentrate. The aquasol concentrate of *Garcinia cambogia* comprises *Garcinia cambogia* fruit rind at a concentration of 725-760 mgml$^{-1}$ of aquasol concentrate.

The excess calories from meals or other food items, which are neither used directly for energy to produce biochemical compounds and structural components, nor stored as glycogen, are usually deposited as body fat by an enzyme ATP-citrate lyase. (−)-Hydroxycitric acid inhibits ATP-citrate lyase enzyme and decreases body fat production.

The aquasol concentrate of *Garcinia cambogia* is prepared using pure and safe mineral water. The unstable lactone form of (−)-hydroxycitric acid is further stabilized with salts such as calcium, magnesium and potassium, which are essential for various biochemical reactions. The extract is produced as a beverage product useful for weight management, obesity, hypercholesterolemia etc.

The aquasol concentrate of *Garcinia cambogia* is prepared from the fruit rinds of *Garcinia cambogia* using a customized processing mechanism. This process involves the water extraction of fruit rind under cold circulation, which retains the phytochemical properties of the component.

The slimming water used to prepare the aqueous extract of *Garcinia cambogia* is specially treated to ensure safety for human consumption. The treatment methods include sand filtration, activated carbon filtration, Ultra-Violet (UV) treatment, reverse osmosis, ozonization. In addition, water is also subjected to mineralization.

The aquasol concentrate of *Garcinia cambogia* is prepared from the cleaned, pulverized and dried fruit rinds of *Garcinia cambogia*. The major phytoconstituent in *Garcinia cambogia* is (−)-hydroxycitric acid. (−)-HCA is a principal acid found to suppress the fatty acid synthesis, lipogenesis, food intake and promotes glycogenesis, gluconeogenesis and induces weight loss.

FIG. 1 illustrates a flow chart for a process of preparation of aquasol concentrate of *Garcinia cambogia*. The process (100) starts at step (101) of extracting the *Garcinia cambogia* fruit rinds using cold circulation of water using cone shaped stainless steel extractor. At step (102), the liquid extract is filtered using a sparkler filter to remove in-soluble components. At step (103), the filtered liquid extract containing the (−)-hydroxycitric acid is adsorbed using ion exchange resins to remove the unwanted compounds. At step (104), the adsorbed (−)-hydroxycitric acid is eluted using potassium hydroxide solution. At step (105), the potassium salt of elute is treated with activated charcoal to remove the impurities. At step (106), the potassium salt of elute is converted to potassium-calcium-magnesium salt by addition of calcium hydroxide and magnesium hydroxide. At step (107), potassium-calcium-magnesium salt of (−)-hydroxycitric acid is concentrated to yield a thick solution having total dissolved solids at the concentration of 25% to 38%. At step (108), the concentrated triple salt complex of (−)-hydroxycitric acid is filtered through cellulose bed to remove suspended impurities. At step (109), an aquasol concentrate of (−)-hydroxycitric acid is adjusted to pH of 5.0 to 6.0.

The aquasol concentrate thus obtained is filled in the polypropylene bottle. The polypropylene bottle containing aquasol concentrate is sterilized by pasteurization. The sterilized aquasol concentrate is subjected to qualitative and quantitative tests using Thin-layer chromatography (TLC), high-performance liquid chromatography (HPLC) and Ultra-violet spectrophotometer to identify the quantity of (−)-hydroxycitric acid. The aqueous extract is further subjected to stability test. The decolorized, deodorized aqueous extract is highly water soluble and is bioavailable in nature.

The aqueous extract of *Garcinia cambogia* showed a shelf-life of minimum 18 months. The quantitative analysis of the aqueous extract of *Garcinia cambogia* showed presence of total dissolved salts of 37.24% w/w, pH 6.10, soluble in water, density of 1.24 gml$^{-1}$ at 25° C. The presence of minor concentration of heavy metals, lead and arsenic complies with the recommended levels. High Performance Liquid Chromatography (HPLC) analysis showed the presence of 27.53 of (−)-hydroxycitric acid.

The slim and aqueous concentrate of *Garcinia cambogia* extract equivalent to 1000 mg of (−)-hydroxycitric acid on dried basis is incorporated into 1.5 liters of packaged drinking water and packed as per the standard norms. 1.5 ml of the concentrate is added to water and consumed daily for effective weight reduction. 1500 mg of *Garcinia cambogia* extract in two to three divided pre-prandial doses per day is recommended for weight management. The slim and aqueous concentrate of *Garcinia cambogia* extract is colorless, odourless and tastes similar to drinking water.

The process of extraction includes the cold circulation method, which effective in retaining the phytochemical properties for better efficacy.

The slim and aqueous concentrate of *Garcinia cambogia* extract is natural, herbal product and consumer friendly dietary supplement for weight management. The triple salt form of (−)-hydroxycitric acid is effective than lactone form of (−)-hydroxycitric acid. *Garcinia cambogia* extract is easily miscible with water or any solution. It is useful in beverage industry, pharmaceutical and is enriched with the optimum range of mineral salts for weight management, hypercholesterolemia etc. *Garcinia cambogia* extract does not contain any synthetic extracts.

The slim and aqueous concentrate of *Garcinia cambogia* extract increases glycogen loading, insulin sensitivity, decreases appetite, inhibits fatty acid synthesis from endogenous glycogen without altering protein synthesis.

We claim:

1. A process for preparation of aquasol concentrate of *Garcinia cambogia*, the process comprising the steps of:
   a. extracting *Garcinia cambogia* fruit rind using cold circulation of water using cone shaped stainless steel extractor;
   b. filtering liquid extract using a sparkler filter to remove one or more in-soluble components;
   c. adsorbing the liquid extract filtrate containing the (−)-hydroxycitric acid using ion exchange resin to remove one or more unwanted compounds;
   d. eluting the adsorbed (−)-hydroxycitric acid using potassium hydroxide solution;
   e. treating the potassium salt of elute with activated charcoal to remove one or more impurities;
   f. converting the potassium salt of elute to potassium-calcium-magnesium salt by addition of calcium hydroxide and magnesium hydroxide;
   g. concentrating a potassium-calcium-magnesium salt of (−)-hydroxycitric acid to yield a thick solution with total dissolved solids at the concentration of 25% to 38%;
   h. filtering the concentrated triple salt complex of (−)-hydroxycitric acid through cellulose bed to remove one or more suspended impurities; and
   i. adjusting the pH of the filtrate aquasol concentrate of (−)-hydroxycitric acid to 5.0 to 6.0.

2. The process as claimed in claim 1, wherein the extraction method using cold circulation retains the phytochemical properties for better efficacy of the aquasol concentrate of *Garcinia cambogia*.

3. The process as claimed in claim 1, wherein the aquasol concentrate of *Garcinia cambogia* is filled in polypropylene bottle and is sterilized by pasteurization.

4. The process as claimed in claim 1, wherein the aquasol concentrate of *Garcinia cambogia* is soluble in water and exhibits bioavailability.

5. The process as claimed in claim 1, wherein the aquasol concentrate of *Garcinia cambogia* at the concentration of 1500 mg is diluted with water and consumed at two pre-prandial doses for weight management.

* * * * *